United States Patent [19]  [11] 4,177,198
Bohen  [45] Dec. 4, 1979

[54] PROCESS FOR PREPARING ALKALINE EARTH METAL MERCAPTIDES

[75] Inventor: Joseph M. Bohen, King of Prussia, Pa.

[73] Assignee: Pennwalt Corporation, Philadelphia, Pa.

[21] Appl. No.: 866,738

[22] Filed: Jan. 3, 1978

[51] Int. Cl.$^2$ .................. C08H 3/00; C07C 69/00; C07C 149/00
[52] U.S. Cl. ..................... 260/399; 260/455 R; 260/583 EE; 260/609 R; 260/609 D; 560/103; 560/124; 560/147; 560/9; 560/18; 560/265; 568/851
[58] Field of Search ............ 260/399, 455 R, 583 EE, 260/609 D, 609 R; 560/103, 124, 147, 9, 18, 265; 568/851

[56] References Cited

U.S. PATENT DOCUMENTS 2,405,713  8/1946  Russell .................................. 568/851
4,115,352  9/1978  Bohen et al. ...................... 260/23 XA

*Primary Examiner*—John F. Niebling

[57] ABSTRACT

A process for preparing alkaline earth metal mercaptides, useful as synergists for organotin stabilizers in halogen containing resins such as polyvinyl chloride, the process comprising preparing an alkaline earth metal alkoxide by reacting the metal oxide or hydroxide with an alcohol and then reacting the alkoxide with a mercaptan to provide the corresponding alkaline earth metal mercaptide, preferably while removing water from the reaction mixtures throughout the process.

18 Claims, No Drawings

PROCESS FOR PREPARING ALKALINE EARTH METAL MERCAPTIDES

BACKGROUND OF THE INVENTION

As described in co-pending U.S. application Ser. No. 799,862 filed May 23, 1977 U.S. Pat. No. 4,115,352, entitled "Heat Stabilizer Composition for Halogenated Resins", certain alkaline earth metal mercaptides are particularly useful as synergists in conjunction with certain sulfur containing organotin or antimony compounds.

In the above cited patent application, the alkaline earth metal mercaptides are prepared in accordance with the following reactions; wherein M is the alkaline earth metal:

$$M + 2R'OH \rightarrow M(OR')_2 + H_2 \uparrow \quad (I)$$

$$M(OR')_2 + 2HSR \rightarrow M(SR)_2 + 2R'OH \quad (II)$$

The economics of carrying out such reactions commercially is less than ideal, as metals, M, are expensive. Other known methods by which certain metal alkoxides may be conveniently prepared are summarized by D. C. Bradley in "Progress in Inorganic Chemistry", Vol. 2 (edited by F. A. Cotton, Interscience Publishers, Inc., New York, N.Y., 1960, pp. 303 ff). However, the only method cited by Bradley for preparing the alkaline earth metal alkoxides involves starting with the metal which is commercially uneconomical.

The oxides and hydroxides (hydrated or anhydrous) of the alkaline earth metals represent a much lower cost source for the metal M than the free metal itself.

The process of this invention provides a process for preparing the desired mercaptide starting from the metallic oxide, MO, or the hydroxide, $M(OH)_2 \cdot xH_2O$.

SUMMARY OF THE INVENTION

The process of this invention provides a simple two-step process for preparing the desired alkaline earth metal mercaptides useful as synergists for organotin stabilizers. The process provides excellent yields at substantial savings over other presently known methods.

The first step of the process is represented by the two equations III and IV below, depending upon whether the starting material is the oxide or the hydroxide of the metal M.

$$MO + 2R'OH \underset{heat}{\rightleftarrows} M(OR')_2 + H_2O \quad (III)$$

or $$M(OH)_2 \cdot xH_2O + 2R'OH \underset{heat}{\rightleftarrows} M(OR')_2 + (x+2)H_2O \quad (IV)$$

wherein:
M is an alkaline earth metal (a group IIa metal of the Periodic Table); and,
R is a hydrocarbon radical having from 1-20 carbon atoms and is selected from the group consisting of alkyl, cycloalkyl, or aralkyl, optionally substituted with inert groups such as halogen, and alkoxy; and x is a number from 0 to 16.

In the second step, the desired alkaline earth metal mercaptide is produced according to the reaction:

$$M(OR')_2 + 2HSR \rightarrow M(SR)_2 + 2R'OH \quad (V)$$

wherein:
R is a hydrocarbon radical (such as alkyl, cycloalkyl, aryl, or mixed alkyl-aryl) of 1–22 carbon atoms, optionally substituted by halogen, —XH, —XR², $$-X-\overset{\overset{Y}{\|}}{C}R^2, \text{ or } -\overset{\overset{Y}{\|}}{C}XR^2$$

where R² is a 1–20 carbon atoms alkyl, alkenyl, cycloalkyl, aryl, or mixed alkyl-aryl group; X and Y are independently selected from O and S.
M is preferably calcium or barium and R' is preferably methyl or ethyl.

The process of the invention is defined as a process for preparing alkaline earth metal mercaptides of the general formula $M(SR)_2$, wherein M is an alkaline earth metal selected from group IIa of the periodic table consisting of barium, calcium magnesium and strontium and R is a hydrocarbon radical having from 1 to 22 carbon atoms and is selected from the group consisting of alkyl, cycloalkyl, aryl and mixed alkylaryl, said hydrocarbon radicals can optionally have a non-interfering substituent selected from the group consisting of halogen, —XH, —XR², $$-X-\overset{\overset{Y}{\|}}{C}R^2 \text{ and } -\overset{\overset{Y}{\|}}{C}-XR^2$$

where R² is a hydrocarbon radical having from 1–20 carbon atoms and is selected from the group consisting of alkyl, alkenyl, cycloalkyl, aryl and mixed alkyl-aryl with the proviso that R² may be further substituted with inert substituents and X and Y are independently selected from the group consisting of oxygen and sulfur, comprising:

(1) forming a mixture in a reactor of:
  (a) a metal oxide of the general formula MO or a metal hydroxide of the formula $M(OH)_2 \cdot xH_2O$, wherein x is a number from 0 to 16; and
  (b) an alcohol of the general formula R'OH wherein R' is a hydrocarbon radical of 1–22 carbon atoms selected from the group consisting of alkyl, cycloalkyl, aryl and mixed alkyl-aryl, with the proviso that said hydrocarbon radical may be optionally substituted with noninterfering inert substituents;
(2) subjecting the mixture of (1) to reaction conditions for sufficient time to form a metal alkoxide $M(OR')_2$ and water;
(3) separating the water from the mixture of (2) to provide the metal alkoxide $M(OR')_2$;
(4) forming a reaction mixture of the metal alkoxide $M(OR')_2$ of (3) and a mercaptan of the general formula HSR;
(5) subjecting the mixture of (4) to reaction conditions for sufficient time to provide the metal mercaptide $M(SR)_2$; and then
(6) separating the metal mercaptide $M(SR)_2$ from the remainder of the mixture of (5).

It is preferred that water be removed from the reaction mixture throughout the process, whether the water be water of reaction or the water of hydration in the case of $M(OH)_2 \cdot xH_2O$ (when x is at least 1) as the starting material. This preferably done with the addition of an inert solvent to the starting solution in step (1). The solvent should be one that forms an azeotrope with water such as toluene, xylene, or heptane. In addition, the inert solvent along with the alcohol in excess, R'OH, acts as a solvent for the reaction.

In step 1(a), any water of hydration is preferably removed prior to the addition of the alcohol R'(OH).

The preferred mercaptan HSR, in step (4) above, is one wherein R is selected from the group:

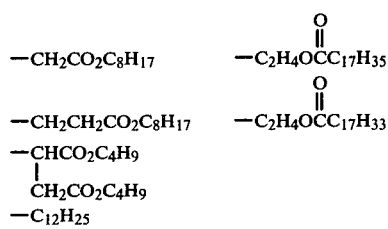

Preferred R' groups for the alcohol R'(OH) in step (1)(b) are alkyl groups of 1–18 carbon atoms with methyl and ethyl being particularly preferred.

The mercaptan HSR can also be added in step (1) along with the alcohol or inert solvent rather than in step (4).

DESCRIPTION OF THE PREFERRED EMBODIMENTS

In the preferred practice of this Invention, the two reactants, that is to say the alkaline earth metal oxide or hydroxide and alcohol (according to reactions III and IV above), are added to the reactor. Sufficient alcohol, R'OH, to react with either starting material employed (and preferably more, the excess acting as a solvent for the reaction), is added. the reaction mixture is heated to the boiling point of the alcohol for a period of time ranging from about 10 minutes to about 5 hours, typically 30 minutes to about 90 minutes to provide the alkoxide $M(OR')_2$. An inert solvent such as benzene, toluene, butyl chloride, butyl ether, carbon tetrachloride, chlorobenzene, 2-chloroethyl ether, chloroform, chloroisopropyl ether, cyclohexane, 2,5-dimethyl furan, 1,4-dioxane, ethyl acetate, hexane, heptane, nonane, isooctane, xylene, etc. (preferably one which forms an azeotrope with water) is added to facilitate the removal of the water resulting from the reaction. The water is removed by distillation so that the reaction (III or IV above) can be driven more completely to the right, thereby increasing yield.

If a hydrate of the metal hydroxide is employed as the starting material, it is generally preferred to remove the water of hydration initially by adding the inert solvent and heating the resulting mixture (i.e., metal hydroxide and solvent) to the boiling point of the solvent for the period of time required to distill off the water of hydration, typically from 0.5 to 3.0 hours. This reduces the amount of water initially in the reaction mixture and provides a shorter reaction time by preventing the establishment of an unfavorable equilibrium. The alcohol is then added and the procedure followed as described above.

The mercaptan, RSH, in reaction V above may be added next, or as a solution with either R'OH or the inert solvent. The temperature of the reaction may range from about 0° C. to the boiling point of the solvent. The preferred temperature range is about 15° C. to about 50° C. The molar ratio of mercaptan to metal alkoxide $M(OR')_2$ is preferably in the stoichiometric amount of 2:1 to avoid a waste of materials.

At the end of the reaction, the reaction mixture is usually clear and colorless. If it is hazy, or if slight precipitate is present, it may be clarified by filtration. The filtrate is then stripped under vacuum to afford the desired alkaline earth metal mercaptide.

If R in the mercaptan is other than alkyl, all water should be removed prior to the addition of the mercaptan to avoid problems of hydrolysis.

EXAMPLE 1

Into a one-liter, three-necked flask equipped with a mechanical stirrer, water condenser and stopper are placed 15.3 g (0.10 mole) of barium oxide and 150 ml of methanol. The resulting solution is heated under reflux for 30 minutes and then cooled to room temperature. Xylene (350 ml) is added and a distillation apparatus attached. The mixture is heated under reflux and 165.5 g of distillate (containing approx. 1.8 g of water) is collected over a period of 2½ hours. The reaction mixture is cooled to room temperature and a solution of 40.9 g (0.2 mole) of isooctyl thioglycolate in 75 ml of methanol is added over a period of 45 minutes. The resulting solution is concentrated under reduced pressure to give an essentially quantitative yield of barium bis(isooctyl thioglycolate).

The same result is obtained when the inert solvent, xylene, is added to the barium oxide and methanol prior to reflux.

EXAMPLE 2

Following the procedure outlined in Example 1 except that calcium oxide is used in place of barium oxide and toluene in place of xylene, there is obtained calcium bis(isooctyl thioglycolate).

EXAMPLE 3

Following the procedure outlined in Example 1 except that 17.14 g (0.10 mole) of barium hydroxide is used in place of barium oxide and toluene in place of xylene, there is obtained in an essentially quantitative yield barium bis(isooctyl thioglycolate).

Anal. Calcd. for $C_{20}H_{38}BaO_4S_2$: $S_{(mercapto)}$, 11.8%; Found: $S_{(mercapto)}$, 11.0%.

EXAMPLE 4

Following the procedure outlined in Example 1 except that strontium hydroxide is used in place of barium oxide and dodecyl mercaptide in place of isooctyl thioglycolate, there is obtained strontium bis(dodecyl mercaptide).

EXAMPLE 5

Into a one-liter, three-necked flask equipped with a thermometer, mechanical stirrer, and a Dean-Stark trap is placed 18.9 g (0.10 mole) of barium hydroxide monohydrate and 350 ml of toluene. The mixture is heated under reflux until the theoretical amount of water of hydration is collected in the Dean-Stark trap, approximately 2 hours. Methanol (260 ml) is added and the Dean-Stark trap is replaced by a distillation apparatus. The mixture is distilled until a pot temperature of 110°–115° C. is reached (approximately 375 g of distillate is collected). The reaction mixture is cooled to room temperature and a solution of 40.9 g (0.2 mole) of isooctyl thioglycolate in 75 ml of methanol is added over a period of 45 minutes. The resulting solution is concentrated under reduced pressure to give an essentially quantitative yield of barium bis(isooctyl thioglycolate).

Anal. Calcd. for $C_{20}H_{38}BaO_4S_2$: $S_{(mercapto)}$, 11.8%; Found: $S_{(mercapto)}$, 11.4%.

EXAMPLE 6

Following the procedure outlined in Example 5 except that barium hydroxide octahydrate is used in place of barium hydroxide monohydrate, heptane in place of toluene, and 2-mercaptoethyl oleate in place of isooctyl thioglycolate, there is obtained barium bis(2-mercaptoethyl oleate).

EXAMPLE 7

Following the procedure outlined in Example 1 except that magnesium hydroxide is used in place of barium oxide and dibutyl mercaptosuccinate in place of isooctyl thioglycolate, there is obtained magnesium bis(dibutyl mercaptosuccinate).

EXAMPLE 8

Following the procedure outlined in Example 5 except that 68.9 g (0.2 mole) of 2-mercaptoethyl stearate is used in place of the isooctyl thioglycolate, there is obtained an essentially quantitative yield of barium bis(2-mercaptoethyl stearate).

EXAMPLE 9

The procedure of Examples 5 and 8 are repeated except that the below listed alcohols are substituted for the $CH_8OH$: ethyl, n-propyl, isopropyl, n-butyl, isobutyl, sec-butyl, tert-butyl, neopentyl, hexyl, octyl, lauryl, oleyl, dodecyl, cyclopentyl, cyclohexyl, cycloheptyl, benzyl, β-phenylethyl, β-phenylpropyl, γ-phenylpropyl, 2-methoxyethyl, 2-chloroethyl, 2-phenoxyethyl, 2-methoxypropyl, 2-butoxypropyl, 2-dimethylaminoethyl, 3-diethylaminopropyl, 2(2'-ethoxyethoxy)-ethyl, p-phenylbenzyl, p-methylbenzyl, o-ethylbenzyl.

For each alcohol results similar to those of Examples 5 and 8 respectively are obtained.

EXAMPLE 10

The procedure of Example 5 is repeated except that the below enumerated R groups are each utilized as the R group in the mercaptan HSR: methyl, ethyl, n-propyl, isopropyl, n-butyl, isobutyl, sec-butyl, tert-butyl, neopentyl, hexyl, octyl, decyl, dodecyl, tridecyl, hexadecyl, octadecyl, cyclopentyl, cyclohexyl, cyclooctyl, benzyl, β-phenylethyl, β-phenylpropyl, γ-phenylpropyl, 2-hydroxyethyl, 2-ethoxyethyl, carboethoxymethyl, carbooctoxymethyl, 1-carbooctoxyethyl, 2-carbooctoxyethyl, 2-dimethylaminoethyl, 2-stearoxyethyl, 2-acetoxyethyl, 2,3-diacetoxypropyl, 2,3-dilauroxypropyl, 2-hydroxy-3-octoxypropyl, 4-methylcyclohexyl, 4-methoxycyclohexyl, 2-methoxycyclopentyl, p-phenylbenzyl, o-methoxybenzyl, phenyl, tolyl, naphthyl, 1,2-dicarbobutoxyethyl, 1,1-dicarbobutoxymethyl, 1-carbobutoxy-2-carbooctoxyethyl, 1-carbomethoxy-1-carbooctoxymethyl, 2-methylmercaptoethyl, 2-thiocarbooctoxymethyl, and thiocarbothiobutoxymethyl.

Results similar to those of Example 5 are obtained for each corresponding mercaptide that is prepared from each mercaptan.

I claim:

1. A process for preparing alkaline earth metal mercaptides of the general formula $M(SR)_2$, wherein M is alkaline earth metal selected from group IIa of the periodic table consisting of barium, calcium, magnesium and strontium and R is a hydrocarbon radical having from 1 to 22 carbon atoms and is selcted from the group consisting of alkyl, cycloalkyl, aryl and mixed alkyl-aryl, said hydrocarbon radicals can optionally have a noninterfering substituent selected from the group consisting of halogen,

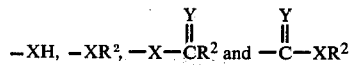

where $R^2$ is a hydrocarbon radical having from 1–20 carbon atoms and is selected from the group consisting of alkyl, alkenyl, cycloalkyl, aryl and mixed alkyl-aryl with the proviso that $R^2$ may be further substituted with inert substituents and X and Y are independently selected from the group consisting of oxygen and sulfur, comprising:

(1) forming a mixture in a reactor of:
   (a) a metal oxide of the general formula MO or a metal hydroxide of the formula $M(OH)_2 \cdot xH_2O$, wherein x is a number from 0 to 16; and
   (b) an alcohol of the general formula R'OH wherein R' is a hydrocarbon radical of 1–22 carbon atoms selected from the group consisting of alkyl, cycloalkyl, aryl, and mixed alkyl-aryl, with the proviso that said hydrocarbon radical may be optionally substituted with noninterfering inert substituents;
(2) subjecting the mixture of (1) to reaction conditions for sufficient time to form a metal alkoxide $M(OR')_2$ and water;
(3) separating the water from the mixture of (2) to provide the metal alkoxide $M(OR')_2$;
(4) forming a reaction mixture of the metal alkoxide $M(OR')_2$ of (3) and a mercaptan of the general formula HSR;
(5) subjecting the mixture of (4) to reaction conditions for sufficient time to provide the metal mercaptide $M(SR)_2$; and then
(6) separating the metal mercaptide $M(SR)_2$ from the remainder of the mixture of (5).

2. The process as defined in claim 1 that includes adding to the mixture of step (1) an inert solvent selected from the group of inert solvents that form an azeotrope with water to facilitate separation of water throughout the process and act as a solvent for the reaction.

3. The process as defined in claim 1 that includes adding to the $M(OH)_2$ of step (1)(a) an inert solvent selected from the group of inert solvents that form an azeotrope with water and then removing any water of hydration that may be present from the metal hydroxide $M(OH)_2 \cdot xH_2O$ prior to addition of the alcohol R'(OH) in step (1)(b).

4. The process as defined in claim 1 wherein in step (1)(a) the metal hydroxide is $Ba(OH)_2 \cdot xH_2O$, wherein x is a number from 1–8 inclusive, the water of hydration from the metal hydroxide is (1)(a) is removed by the addition of an inert solvent that forms an azeotrope with water and then distilling under reflux; and then the alcohol R'(OH) of (1)(b) is added, R' being methyl or ethyl.

5. The process as defined in claim 1 wherein in step (4), R in the general formula HSR is selected from the group consisting of:

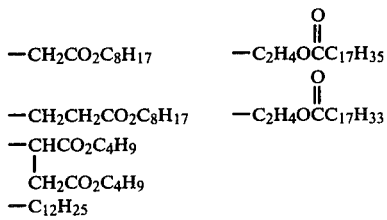

6. The process as defined in claim 1 wherein: M is calcium or barium, R' is methyl or ethyl; and, R is selected from the group consisting of

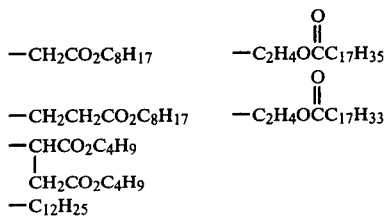

7. The process as defined in claim 1 wherein: M is calcium or barium; R' is an alkyl group of 1-8 carbon atoms; and R is selected from the group consisting of:

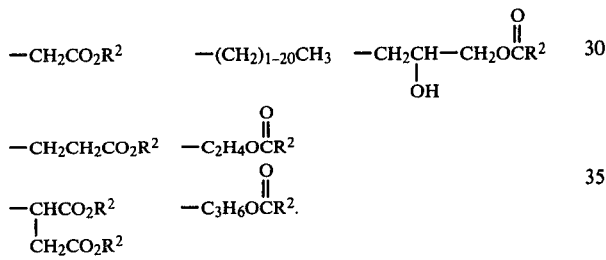

8. The process as defined in claim 1 wherein in step (1)(a) the water of hydration is removed from the $M(OH)_2 \cdot xH_2O$ when x is one or more, prior to the addition of the alcohol R'OH of step (1)(b).

9. The process as defined in claim 1 wherein in step (1)(b), the optional inert noninterfering substituents with which R' can be substituted are selected from the group consisting of phenyl, methoxy, butyoxy, ethoxy, amino and benzyl.

10. The process as defined in claim 2 wherein the inert solvent is selected from the group consisting of xylene, toluene, cyclohexane and heptane.

11. A process for preparing alkaline earth metal mercaptides of the general formula $M(SR)_2$, wherein M is an alkaline earth metal selected from group IIa of the periodic table consisting of barium, calcium, magnesium and strontium and R is a hydrocarbon radical having from 1 to 22 carbon atoms and is selected from the group consisting of alkyl, cycloalkyl, aryl and mixed alkyl-aryl, said hydrocarbon radicals can optionally have a noninterfering substituent selected from the group consisting of halogen, —XH, —XR$^2$,

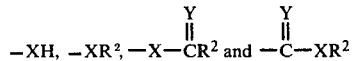

where R$^2$ is a hydrocarbon radical having from 1-20 carbon atoms and is selected from the group consisting of alkyl, alkenyl, cycloalkyl, aryl and mixed alkyl-aryl with the proviso that R$^2$ may be further substituted with inert substituents and X and Y are independently selected from the group consisting of oxygen and sulfur, comprising:

(1) forming a mixture in a reactor of:
 (a) a metal oxide of the general formula MO or a metal hydroxide of the formula $M(OH)_2 \cdot xH_2O$, wherein x is a number from 0 to 16;
 (b) an alcohol of the general formula R'OH wherein R' is a hydrocarbon radical of 1-22 carbon atoms selected from the group consisting of alkyl, cycloalkyl, aryl and mixed alkyl-aryl, with the proviso that said hydrocarbon radical may be optionally substituted with noninterfering inert substituents; and
 (c) a mercaptan of the general formula HSR, (2) subjecting the mixture of (1) to reaction conditions for sufficient time to first form a metal alkoxide $M(OR')_2$ in situ, and then a final reaction product of the desired mercaptide $M(SR)_2$ while removing water from the reaction mixture.

(3) separating the metal mercaptide $M(SR)_2$ from the remainder of the mixture of (2).

12. The process as defined in claim 11 that includes adding to the mixture of step (1) an inert solvent selected from the group of inert solvents that form an azeotrope with water to facilitate separation of water throughout the process and act as a solvent for the reaction.

13. The process as defined in claim 11 that includes adding to the $M(OH)_2$ of step (1)(a) an inert solvent selected from the group of inert solvents that form an azeotrope with water and then removing any water of hydration that may be present from the metal hydroxide $M(OH)_2 \cdot xH_2O$ prior to addition of the alcohol R'(OH) in step (1)(b).

14. The process as defined in claim 11 wherein in step (1)(a) the metal hydroxide is $Ba(OH)_2 \cdot xH_2O$, wherein x is a number from 1-8 inclusive, the water of hydration from the metal hydroxide in (1)(a) is removed by the addition of an inert solvent that forms an azeotrope with water and then distilling under reflux; and then the mercaptan HSR and the alcohol R'(OH) are added, R' being methyl or ethyl, 15. The process as defined in claim 11 wherein in step (1)(c), R in the general formula HSR is selected from the group consisting of:

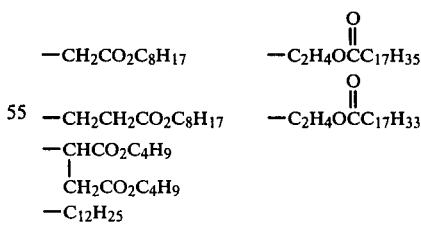

16. The process as defined in claim 11 wherein: M is calcium or barium; R' is an alkyl group of 1-8 carbon atoms; and R is selected from the group consisting of:

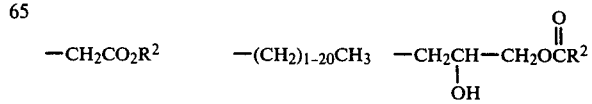

-continued

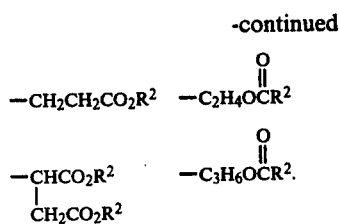

17. The process as defined in claim 11 wherein in step (1)(a) the water of hydration is removed from the $M(OH)_2 \cdot xH_2O$ when x is one or more, prior to the addition of the alcohol R'OH and the mercaptan HSR.

18. The process as defined in claim 11 wherein in step (1)(b), the optional inert noninterfering substituents with which R' can be substituted are selected from the group consisting of phenyl, methoxy, butyoxy, ethoxy, amino and benzyl.

* * * * *